US008696427B2

(12) United States Patent
Hein

(10) Patent No.: US 8,696,427 B2
(45) Date of Patent: *Apr. 15, 2014

(54) VARIABLE PAYOUT PERCENTAGE GAMING SYSTEM

(75) Inventor: Marvin A. Hein, Las Vegas, NV (US)

(73) Assignee: Bally Gaming, Inc., Las Vegas, NV (US)

( * ) Notice: Subject to any disclaimer, the term of this patent is extended or adjusted under 35 U.S.C. 154(b) by 92 days.

This patent is subject to a terminal disclaimer.

(21) Appl. No.: 13/454,657

(22) Filed: Apr. 24, 2012

(65) Prior Publication Data

US 2012/0208626 A1 Aug. 16, 2012

Related U.S. Application Data

(63) Continuation of application No. 12/956,312, filed on Nov. 30, 2010, now Pat. No. 8,191,752.

(51) Int. Cl.
*G07F 17/32* (2006.01)

(52) U.S. Cl.
USPC ............... 463/16; 463/20; 463/25; 463/29

(58) Field of Classification Search
USPC ............................... 463/16, 20, 25, 29
See application file for complete search history.

(56) References Cited

U.S. PATENT DOCUMENTS 6,852,031 B1 * 2/2005 Rowe .......................... 463/29
8,172,661 B1 * 5/2012 Hein .......................... 463/16

* cited by examiner

*Primary Examiner* — Omkar Deodhar
(74) *Attorney, Agent, or Firm* — Marvin Hein

(57) ABSTRACT

A gaming device adjusts the payout percentage of the gaming device once a player initiates game play. In one embodiment, the payout percentage of the gaming device increases the longer a player plays on the gaming device. In other embodiments, the payout percentage increases as a result of a player-triggered event. Accordingly, player excitement is heightened by the opportunity to obtain a greater payout.

5 Claims, 2 Drawing Sheets

VARIABLE PAYOUT PERCENTAGE GAMING SYSTEM

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

This invention relates generally to gaming apparatus, and more particularly, to gaming apparatus wherein the payout percentage of the gaming apparatus may be adjusted during game play.

BACKGROUND OF THE INVENTION

Many different types of gaming devices have developed over time to add or to maintain interest in gaming devices. For example, in some slot machines the display windows show more than one adjacent symbol on each reel, thereby allowing multiple row betting. Other types of slot machines have also been developed to increase player interest that include "second chance" games. Typically, "second chance" games try to maintain player interest from a first game segment to a second game segment by providing the player with another opportunity to win.

However, there is a continuing need for additional slot machine variants that provide a player with enhanced excitement and diversity of game play, without departing so far from the original slot machine gaming concept that player comfort is lost. Further, there is a continuing need for a gaming machine that provides increased player excitement due to the visual entertainment that occurs specifically in response to the player's actions. Accordingly, those skilled in the art have long recognized the need for a gaming machine that addresses these issues.

SUMMARY OF THE INVENTION

Briefly, and in general terms, the various embodiments are directed to a gaming machine for maintaining or increasing player interest. In one embodiment, the gaming machine includes a means for enabling a player to play a game and a means for adjusting the payout percentage of the gaming machine when a player has actuated a trigger. In another embodiment, the gaming machine includes a means for displaying the payout percentage of the gaming machine. Accordingly, player interest is maintained or increased, as the player is able to see the payout percentage of the game increase.

In another aspect, various methods are directed to maintaining player interest in a gaming machine. According to one method, the method includes: providing a gaming machine having a display for a payout percentage of the gaming machine; adjusting the payout percentage of the gaming machine once game play has been initiated; and resetting the payout percentage to a baseline value once game play is terminated. In one method, the payout percentage is increasing as a function of the amount of time the gaming machine is played. In other methods, the payout percentage increases as a result of various triggers such as, but not limited to, amount wagered by a player, a player's rating, inserting a player tracking device, or playing a bonus game.

Other features and advantages of the present invention will become apparent from the following detailed description, taken in conjunction with the accompanying drawings, which illustrate by way of example, the features of the present invention.

DETAILED DESCRIPTION OF THE PREFERRED EMBODIMENTS

The various embodiments disclosed herein relate to a gaming device that adjusts the payout percentage of the gaming device once a triggering event has been initiated. As defined herein the payout percentage of a gaming device is the long-term payout percentage of the gaming machine based upon the amount of money wagered. For instance, a 98% payout machine, over the long-term, will pay out 98 cents of every dollar that is wagered on a particular gaming machine. According to one embodiment, player excitement is heightened by the opportunity to obtain a higher payout based upon a triggering event such as, but not limited to, the duration of game play. That is, the payout percentage of the game increases the longer a player plays on the gaming device.

Figure 1:
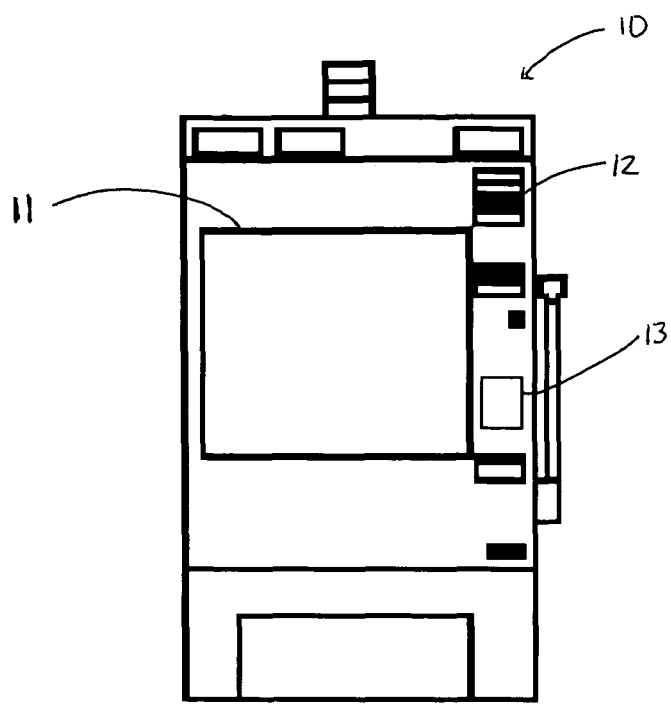
FIG. 1 illustrates a front view of one embodiment of a gaming machine.

FIG. 1 illustrates one embodiment of a gaming machine 10 that includes a gaming display 11, a playing tracking interface 12, and a payout display 13 showing the payout percentage of the game machine. As those skilled in the art will appreciate, the gaming machine 10 may be used to play slot-type games, keno, blackjack, poker, video games or any other type of games.

Figure 2:
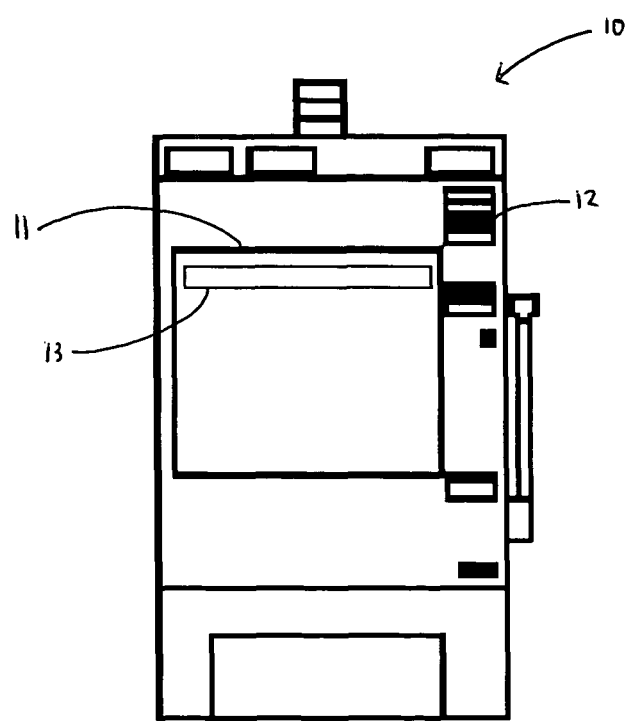
FIG. 2 illustrates a front view of another embodiment of the gaming machine.

According to one embodiment, the payout display 13 may show the incremental increase in the payout percentage of the gaming machine (i.e., 0.0, 0.1 . . . 10.0%). In another embodiment, the payout display 13 may show the overall payout percentage (i.e., 90.0 . . . 100.0%). In another embodiment, lights, flashing lights, audio, graphic video images, or the like can be associated with the payout display 13. For instance, in one embodiment, the payout display 13 may notify the player that the maximum payout has been achieved. In yet another embodiment, the payout display 13 may be a distinct component from the main gaming display 11. In another embodiment, the payout display 13 may be an integral part of the main gaming display 11, e.g., as shown in FIG. 2. In yet another embodiment, the gaming machine 10 may not include a display showing the payout percentage of the gaming machine. Accordingly, the gaming machine merely may be advertised as a gaming machine wherein the payout percentage is adjustable.

According to one embodiment, the gaming machine includes a means for adjusting the payout percentage of the gaming machine. The means for adjusting the payout percentage may be a processor. The adjustment means may increase, decrease or reset the payout percentage of the game. In one embodiment, the adjustment means is contained within the gaming machine. In an alternate embodiment, the adjustment means may be contained within a central system, wherein each gaming machine is networked or otherwise in communication with a central system.

In one method of maintaining or increasing player interest in a gaming device, the method is implemented by using a gaming device having an adjustable payout percentage. Generally, the payout percentage is adjustable upon the occurrence of a triggering event. For example, such triggers include, but are not limited to, the passage of a predetermined amount of time, inserting a player tracking device into the gaming device, status or number of points on a player tracking device that has been inserted into the gaming device, or a particular time, day, week, or month. In one method, the increase in the payout percentage of the gaming device is a function of time. That is, the longer the player plays on the gaming device, the greater the payout percentage. In one method, the payout percentage increases at a linear rate with respect to a particular time interval. For instance, the payout percentage may increase 0.001% for every second a player is playing a particular gaming machine. In another method, the payout percentage of the gaming machine may increase at a non-linear rate with respect to a particular time interval. For instance, the payout percentage may increase at an exponential rate with respect to a particular time interval. In yet another method, the payout percentage increases in a lock-step rate with respect with a particular time interval. For instance, according to one method, the payout percentage may increase 1% every 90 second. As those skilled in the art will appreciate, changes in the payout rate and payout percentage amount may be varied depending upon various parameters set by the manufacturer or casino.

In another method of maintaining or increasing player interest in a gaming device, the trigger for increasing the payout percentage may be based upon the number of games played within a particular period of time. For instance, the payout percentage will increase at a more rapid rate if a player were to play more games rather than fewer over a period of time. hi yet another method, the trigger for increasing payout percentage may be based upon the number of maximum bets placed by a player. For instance, a greater frequency of maximum bets over a period of time will result in the increase of the payout percentage of the gaming machine. Alternatively, in another method, the payout percentage may increase only when a maximum bet is placed.

In another method, an additional trigger may accelerate the rate of increase of the payout percentage of the gaming device. For instance, in one method, the trigger may be obtaining or achieving a bonus game. Alternatively, in one method, a prize of a bonus game may be achieving maximum payout or an incremental increase in the payout percentage of the gaming machine. In another method, acceleration of the rate of increase of the payout percentage may be obtained if a player is playing a certain number of maximum bets. In yet another method, acceleration in the increase in payout percentage may occur if a "frequent" player having a particular player rating is playing on the gaming machine. Accordingly, a "high roller" may be able to achieve maximum payout quicker than a casual gambler. In yet another method, the increase in the payout percentage may be accelerated depending on a particular trigger such as, but not limited to, a particular time, day, week, or month. Accordingly, the rate of increase in the payout percentage may be greater during peak hours thereby maintaining or increasing a player's interest in the gaming machine.

Alternatively, as those skilled in the art will appreciate, the rate of increase of the payout percentage of the gaming machine may be decelerated. For instance, in one method, large delays between plays/wagers may slow the rate at which the payout percentage increases. The delay interval may be adjustable and set by either the casino or the manufacturer.

In another method, the payout percentage is reset to a baseline value. As those skilled in the art will appreciate, a casino or the manufacturer of the gaming device may set the baseline value. In one method, the payout percentage may be reset to the baseline value once a player terminates his gaming session at a particular gaming machine. In another method, the payout percentage may be reset to the baseline value when a player removes his player-tracking device from the gaming machine. In yet another method, the payout percentage may be reset to the baseline value after a defined period of time. In alternate methods, the payout percentage may be reset to a value greater than the baseline value. For instance, in one method, the payout percentage may be set at a value greater than the baseline when a frequent player inserts his/her player-tracking device into the gaming device.

Furthermore, the various methodologies described above are provided by way of illustration only and should not be construed to limit the invention. Those skilled in the art will readily recognize various modifications and changes may be made to the disclosed embodiments without departing from the true spirit and scope of the invention. Accordingly, it is not intended that the invention be limited, except as by the appended claims.

What is claimed is:

1. A gaming system for maintaining player interest in a gaming machine, comprising:
   a gaming machine;
   a display associated with the gaming machine, wherein the display indicates a current payout percentage of the gaming machine;
   a player tracking device associated with the gaming machine;
   a triggering mechanism for increasing the current payout percentage of the gaming machine as a function of time the gaming machine is played.

2. The gaming system of claim 1 wherein the triggering mechanism is associated with the gaming machine.

3. The gaming system of claim 1 wherein the gaming machine is in communication with a central system.

4. The gaming system of claim 3 wherein the triggering mechanism is associated with the central system.

5. The gaming system of claim 1 wherein the gaming machine is not coupled to a central system.

* * * * *